United States Patent [19]

Post et al.

[11] Patent Number: 4,640,766

[45] Date of Patent: Feb. 3, 1987

[54] PROCESS FOR THE PREPARATION OF HYDROCARBONS

[75] Inventors: Martin F. M. Post, Houston, Tex.; Swan T. Sie; Ernst J. R. Sudhölter, both of Amsterdam, Netherlands

[73] Assignee: Shell Oil Company, Houston, Tex.

[21] Appl. No.: 725,189

[22] Filed: Apr. 19, 1985

[30] Foreign Application Priority Data

Apr. 25, 1984 [NL] Netherlands ......................... 8401332

[51] Int. Cl.$^4$ ............................................. C10G 47/00
[52] U.S. Cl. ..................... 208/111; 208/112; 208/950; 423/656; 518/704; 518/714; 518/715
[58] Field of Search ............. 208/108, 111, 950, 112; 518/714, 715, 702, 704; 423/656, 652

[56] References Cited

U.S. PATENT DOCUMENTS

| | | | |
|---|---|---|---|
| 3,904,744 | 9/1975 | Pagel | 423/652 |
| 4,098,339 | 7/1978 | Weisz et al. | 518/704 |
| 4,279,830 | 7/1981 | Haag et al. | 208/950 |
| 4,471,145 | 9/1984 | Chu et al. | 208/950 |
| 4,492,772 | 1/1985 | Ball et al. | 518/714 |
| 4,499,209 | 2/1985 | Hoek et al. | 518/704 |
| 4,500,417 | 2/1985 | Chen et al. | 208/950 |
| 4,522,939 | 6/1985 | Minderhoud et al. | 502/332 |

*Primary Examiner*—John Doll
*Assistant Examiner*—Anthony McFarlane

[57] ABSTRACT

$C_4^-$ hydrocarbons are converted into syngas with a $H_2/CO$ molar ratio between 0.25 and 2.25 by reforming at a pressure above 10 bar in the presence of specified amounts of carbon dioxide and steam followed by conversion of the syngas into $C_5^+$ hydrocarbons over a cobalt-containing catalyst or a catalyst combination comprising a cobalt-containing catalyst and having CO-shift activity.

24 Claims, No Drawings

PROCESS FOR THE PREPARATION OF HYDROCARBONS

FIELD OF THE INVENTION

The invention relates to a process for the preparation of hydrocarbons having at least five carbon atoms per molecule.

BACKGROUND OF THE INVENTION

Hydrocarbons with at least five carbon atoms per molecule (hereinafter referred to as "$C_5+$ hydrocarbons") can be prepared from hydrocarbons having at most four carbon atoms per molecule (hereinafter referred to as "$C_4-$ hydrocarbons") by a two-step process in which the $C_4-$ hydrocarbons are converted in the first step by steam reforming into a mixture of carbon monoxide and hydrogen, which mixture is subsequently converted in the second step into a mixture of hydrocarbons consisting substantially of $C_5+$ hydrocarbons by contacting it at elevated temperature and pressure with a catalyst. The reaction which takes place in the second step of the process is known in the literature as the Fischer-Tropsch hydrocarbon synthesis. Catalysts often used for the purpose comprise one or more metals from the iron group, together with one or more promoters, and a carrier material. These catalysts can suitably be prepared by the known techniques, such as precipitation, impregnation, kneading and melting. The products which can be prepared by using these catalysts usually have a very wide range of molecular weight distribution and, in addition to branched and unbranched paraffins, often contain considerable amounts of olefins and oxygen-containing organic compounds. Usually only a minor portion of the products obtained is made up of middle distillates. Of these middle distillates not only the yield but also the pour point is unsatisfactory. Therefore, the direct conversion of $H_2/CO$ mixtures according to Fischer-Tropsch is not a very attractive route for the production of middle distillates on a technical scale.

In this patent application "middle distillates" should be taken to be hydrocarbon mixtures whose boiling range corresponds substantially with that of the kerosene and gas oil fractions obtained in the conventional atmospheric distillation of crude mineral oil. The middle distillate range lies substantially between about 150° and 360° C.

Recently a class of Fischer-Tropsch catalysts was found which has the property of yielding a product in which only very minor amounts of olefins and oxygen-containing organic compounds occur and which consists virtually completely of unbranched paraffins, a considerable portion of which paraffins boils above the middle distillate range. It has been found that the high-boiling part of this product can be converted in high yield into middle distillates by hydrocracking. As feed for the hydrocracking, at least the part of the product is chosen whose initial boiling point lies above the final boiling point of the heaviest middle distillate desired as end product. The hydrocracking, which is characterized by a very low hydrogen consumption, leads to middle distillates with a considerably better pour point than those obtained in the direct conversion of a $H_2/CO$ mixture according to Fischer-Tropsch.

The Fischer-Tropsch catalysts belonging to the above-mentioned class contain silica, alumina or silica-alumina as carrier material and cobalt together with zirconium, titanium and/or chromium as catalytically active metals, in such quantities that the catalysts comprise about 3–60 pbw of cobalt and about 0.1–100 pbw of zirconium, titanium and/or chromium per 100 pbw of carrier material. The catalysts are prepared by depositing the metals involved on the carrier material by kneading and/or impregnation. For further information on the preparation of these catalysts by kneading and/or impregnation, reference may be made to Netherlands Patent Application No. 8301922, which is commonly-assigned copending U.S. patent application, Ser. No. 594.618, filed Mar. 29, 1984, now U.S. Pat. No. 4,522,939, issued June 11, 1985.

Although the use of the afore-defined cobalt catalysts for the conversion of $H_2/CO$ mixtures yields a product whose high-boiling part can be converted in a simple manner and in high yield into middle distillates, the use of these catalysts in the second step of the two-step process described hereinabove is attended with a number of drawbacks. As described hereinbefore the conversion of the $C_4-$ hydrocarbons in the first step can be carried out by steam reforming. With a view to the reactions which occur during the conversion of the $C_4-$ hydrocarbons and in order to minimize carbonization of the catalyst used, this conversion should be carried out by using a steam/hydrocarbon ratio higher than about 1 g mol/g atom C. The drawbacks attached to the use of the present cobalt catalysts in the second step combined with a conversion of the $C_4-$ hydrocarbons by steam reforming in the first step are connected with the fact that this conversion of the $C_4-$ hydrocarbons yields a $H_2/CO$ mixture having a $H_2/CO$ molar ratio which is considerably higher than about 2. This can be suitably demonstrated with the aid of the development of the reaction when methane is used as feed. In the steam reforming of methane two reactions occur, viz. a main reaction $CH_4 + H_2O \rightarrow CO + 3H_2$ and a side reaction $CO + H_2O \rightarrow CO_2 + H_2$. This reaction development, when $H_2O/CH_4$ molar ratios between about 2 and about 3 which are generally used in practice are applied, leads to $H_2/CO$ mixtures having $H_2/CO$ molar ratios between about 3.8 and about 4.5. It should be noted here that with the present cobalt catalysts the $H_2 + CO$ conversion is smaller according as the $H_2 + CO$ molar ratio of the $H_2/CO$ mixture supplied varies more from 2, and that in addition their $C_5+$ selectivity is lower according as the $H_2/CO$ mixture supplied has a higher $H_2/CO$ molar ratio. Consequently, when the present cobalt catalysts are used for the conversion of a $H_2/CO$ mixture prepared by steam reforming, this leads to both a low $H_2 + CO$ conversion and a low $C_5+$ selectivity. Therefore, in view of the high $H_2/CO$ molar ratio of the $H_2/CO$ mixture formed therein, steam reforming is not very suitable to be used for the preparation of the feed for the present cobalt catalyst.

$H_2/CO$ mixtures having considerably lower $H_2/CO$ molar ratios than when steam reforming is used can be prepared by starting from $C_4-$ hydrocarbons and carrying out the conversion in the presence of carbon dioxide. This so-called carbon dioxide reforming, which, for the same reasons as given for the steam reforming, should be carried out by using a carbon dioxide/hydrocarbon ratio higher than about 1 g mol/g atom C. yields a $H_2/CO$ mixture having a $H_2/CO$ molar ratio which is considerably lower than about 2. As in the case with the steam reforming, this can suitably be demonstrated with the aid of the development of the reaction when methane is used as feed. In the carbon dioxide reforming of methane two reactions occur, viz. a main reaction $CH_4+CO_2\rightarrow 2CO+2H_2$ and a side reaction $H_2+CO_2\rightarrow H_2O+CO$. This reaction development, when $CO_2/CH_4$ molar ratios between about 1.5 and about 2 which are generally used in practice are applied, leads to $H_2/CO$ mixtures having $H_2/CO$ molar ratios between about 0.70 and about 0.64. Although replacing steam reforming with carbon dioxide reforming in the first step of the two-step process wherein the present cobalt catalysts are used in the second step offers a solution to the low $C_5{}^+$ selectivity problem (since the cobalt catalysts show a higher $C_5{}^+$ selectivity according as the $H_2/CO$ molar ratio of the feed is lower), said replacement has no influence on the low $H_2+CO$ conversion problem (caused by a $H_2/CO$ molar ratio of the feed which varies considerably from 2) and gives rise to another problem. To solve these two problems a solution has now been found. High conversions of low-hydrogen $H_2/CO$ mixtures using the present cobalt catalysts can be achieved by using these catalysts in a catalyst combination which has CO-shift activity. The fresh problem mentioned above is connected with the need of carrying out the two steps of the two-step process at substantially the same pressure in order to obviate compression of large gas volumes. Since the hydrocarbon synthesis over the cobalt catalyst of the second step requires a pressure higher than 10 bar, a corresponding high pressure must also be used in the first step. However, a drawback of the carbon dioxide reforming carried out at a high pressure is its low conversion. For instance, the carbon dioxide reforming of methane at a pressure of about 20 bar and a $CO_2/CH_4$ molar ratio of about 2 yields a $H_2/CO$ mixture having a $H_2/CO$ molar ratio of about 0.64 at a methane conversion of not more than about 50%. This drawback can be taken away by carrying out the reforming in the presence of both carbon dioxide and steam. For instance, the above-described reforming of methane in the presence of carbon dioxide at a pressure of about 20 bar and a $CO_2/CH_4$ molar ratio of about 2 in the presence of a quantity of steam corresponding with a $H_2O/CO$ molar ratio of about 0.25 leads to an increase in methane conversion of from about 50 to about 91%, while the $H_2/CO$ molar ratio of the $H_2/CO$ mixture produced only increases from about 0.64 to about 0.66. More generally, it has been found that $H_2/CO$ mixtures whose $H_2/CO$ molar ratios may lie between about 0.25 and about 2.25 at choice can be prepared in high yield by reforming $C_4{}^-$ hydrocarbons at a pressure higher than about 10 bar in the presence of carbon dioxide and steam, provided that the following requirements are met (1) the carbon dioxide/hydrocarbon ratio (a) should be higher than about 0.2 but lower than about 10 g mol $CO_2$/g atom C, (2) the steam/hydrogen ratio (b) should be higher than about 0.1 but lower than about 1 g mol $H_2O$/g atom C, and (3) the carbon dioxide/steam ratio should be chosen such as to meet the requirement $(2\times a+3\times b)>3$.

By using the afore-described reforming as the first step of the two-step process for the preparation of $C_5{}^+$ hydrocarbons from $C_4{}^-$ hydrocarbons while using the present cobalt catalysts in the second step and at a pressure which corresponds substantially with that used in the first step, $C_5{}^+$ hydrocarbons can be prepared according to this two-step treatment in high yield and with high selectivity, provided that if the $H_2/CO$ mixture prepared in the first step has a $H_2/CO$ molar ratio lower than about 1.5, the cobalt catalyst should be used in a catalyst combination which has CO-shift activity.

SUMMARY OF THE INVENTION

The present patent application therefore relates to a process for the preparation of $C_5{}^+$ hydrocarbons from $C_4{}^-$ hydrocarbons, in which $C_4{}^-$ hydrocarbons are converted at a pressure higher than about 10 bar by reforming in the presence of carbon dioxide and steam into a mixture of carbon monoxide and hydrogen having a $H_2/CO$ molar ratio between about 0.25 and about 2.25 by using a carbon dioxide/hydrocarbon ratio (a) higher than about 0.1 but lower than about 10 g mol $CO_2$/g atom C, a steam/hydrocarbon ratio (b) higher than 0.1 but lower than 1 g mol $H_2O$/g atom C and such a carbon dioxide/steam ratio that $(2\times a+3\times b)>3$, in which the mixture of carbon monoxide and hydrogen thus prepared is converted into a mixture of hydrocarbons substantially consisting of $C_5{}^+$ hydrocarbons by contacting it at an elevated temperature and a pressure substantially corresponding with that used in the reforming with a cobalt catalyst comprising about 3-60 pbw of cobalt and about 0.1-100 pbw of at least one other metal chosen from the group formed by zirconium, titanium, and chromium, per 100 pbw of silica, alumina or silica-alumina, which catalyst has been prepared by kneading and/or impregnation, and in which the cobalt catalyst is used in a catalyst combination which has CO-shift activity if the $H_2/CO$ mixture has a $H_2/CO$ molar ratio lower than about 1.5.

DESCRIPTION OF THE PREFERRED EMBODIMENTS

In the process according to the invention the starting material may be a feed which consists substantially of one or more $C_4{}^-$ hydrocarbons or a feed which, in addition to $C_4{}^-$ hydrocarbons, comprises carbon dioxide. It should be noted in this connection that natural gas, which where hydrocarbons are concerned consists mainly of methane, can contain up to about 75 %vol. of carbon dioxide. Examples of $C_4{}^-$ hydrocarbons which alone or in admixture can be present in the feed are methane, ethane, propane, butane and isobutane. Preferably, the process is applied to a feed in which the $C_4{}^-$ hydrocarbons consist substantially of methane. Special preference is given to natural gas as feed and more particular to carbon dioxide-contaminated natural gas.

The reforming according to the invention can be carried out by contacting the hydrocarbons to be converted together with carbon dioxide and steam at a temperature of about 500°-1200° C. and a pressure of about 10-100 bar with a catalyst comprising one or more metals from the iron group supported on a carrier. The reforming is preferably carried out at a temperature of about 700°-1000° C., a pressure of about 10-75 bar and by using a nickel-containing catalyst. In order to prevent the formation of carbon deposits on the catalyst and to remove deposits already formed from the catalyst by conversion into CO, it is preferred to use a catalyst comprising an alkali metal, in particular potassium. In order to prevent the catalyst from sintering, it is moreover preferred to use a catalyst comprising an alkaline earth metal, in particular calcium. If the $C_4{}^-$ hydrocarbons in the feed consist largely or wholly of hydrocarbons containing two or more carbon atoms per molecule, it is preferred to use a catalyst having cracking activity. Cracking activity may be imparted to the catalyst by the use of a silica-alumina as carrier material.

The reforming according to the invention is carried out in the presence of both carbon dioxide and steam, which can be fed to the process from external sources. As described hereinbefore, the process according to the invention can very suitably be applied to a feed which by its nature contains carbon dioxide, so that at least part of the carbon dioxide requirement of the reforming is met. Use can further be made of carbon dioxide and steam which are found in the reaction products of the process according to the invention. Carbon dioxide and steam find their way into the reaction product of the reforming as a result of the fact that the reforming is not a complete reaction, so that even when a stoichiometric quantity is used, a minor portion of the quantity used will be found in the reaction product in the original state. Since in the reforming the total quantity of carbon dioxide and steam used is larger than the stoichiometrically required quantity, the amount used in excess will also be found in the reaction product. It is true that in the reforming there is a minor occurrence of side reactions by which some carbon dioxide and steam is withdrawn from the reaction with the hydrocarbon feed, but these side reactions in themselves yield steam or carbon dioxide as reaction product. Carbon dioxide and steam occur in the reaction product of the hydrocarbon synthesis as well. For in the hydrocarbon synthesis according to the equation $CO+2H_2 \rightarrow -(CH_2)- + H_2O$ a considerably amount of steam is formed as byproduct. And minor quantities of carbon dioxide can find their way into the reaction product of the hydrocarbon synthesis by the occurrence of side reactions. In the process according to the invention, preference is given to at least part of the steam and/or carbon dioxide present in the reaction products being separated therefrom and being recycled to the reforming.

The reforming is preferably carried out by using a carbon dioxide/hydrocarbon ratio (a) higher than about 0.3 and lower than about 4 g mol $CO_2$/g atom C and a steam/hydrocarbon ratio (b) higher than about 0.2 and lower than about 0.8 g mol $H_2O$/g atom C.

In the process of the invention, use is preferably made of the cobalt catalysts which form the subject matter of Netherlands Patent Application No. 8301922, which is commonly-assigned copending U.S. patent application, Ser. No. 594,618, filed Mar. 29, 1984, now U.S. Pat. No. 4,522,939, issued June 11, 1985. They are catalysts which satisfy the relation:

$$(3+4R) > (L/S) > (0.3+0.4R),$$

wherein
L=the total quantity of cobalt present on the catalyst, expressed as mg Co/ml catalyst,
S=the surface area of the catalyst, expressed as $m^2$/ml catalyst, and
R=the weight ratio of the quantity of cobalt deposited on the catalyst by kneading to the total quantity of cobalt present on the catalyst.

The preparation of the cobalt catalysts which are used in the hydrocarbon synthesis is preferably carried out by one of the three procedures mentioned hereinafter:
(a) first cobalt is deposited in one or more steps by impregnation and subsequently the other metal is deposited in one or more steps, also by impregnation,
(b) first the other metal is deposited in one or more steps by impregnation and subsequently the cobalt is deposited in one or more steps, also be impregnation, and
(c) first cobalt is deposited in one or more steps by kneading and subsequently the other metal is deposited in one or more steps by impregnation.

In the process according to the invention, use is preferably made of cobalt catalysts containing about 15–50 pbw of cobalt per 100 pbw of carrier. The preferred quantity of other metal present in the cobalt catalysts depends on the way in which this metal has been deposited. In the case of catalysts where first cobalt has been deposited on the carrier, followed by the other metal, preference is given to catalysts containing about 0.1–5 pbw of the other metal per 100 pbw of carrier. In the case of catalysts where first the other metal has been deposited on the carrier, followed by the cobalt, preference is given to catalysts containing about 5–40 pbw of the other metal per 100 pbw of carrier. Preference is given to zirconium as the other metal and to silica as carrier material. Preparatory to being suitable for use the cobalt catalysts should be activated. This activation can suitably be carried out by contacting the catalyst at a temperature between about 200° and about 350° C. with hydrogen or a hydrogen-containing gas.

In the process of the invention the hydrocarbon synthesis is preferably carried out at a temperature of about 125°–350° C. and in particular of about 175°–275° C. and a pressure of about 10–100 bar and in particular of about 10–75 bar.

In the process of the invention the reforming yields a $H_2/CO$ mixture whose $H_2/CO$ molar ratio may vary between about 0.25 and about 2.25. If the $H_2/CO$ molar ratio of the $H_2/CO$ mixture is lower than about 1.5, the cobalt catalyst should be used in a catalyst combination which has CO-shift activity. Although for the conversion of $H_2/CO$ mixtures with a $H_2/CO$ molar ratio between about 1.5 and about 2.25 the use of the cobalt catalyst per se will do, it is preferred even for the conversion of $H_2/CO$ mixtures with a $H_2/CO$ molar ratio between about 1.5 and about 1.75 to use the afore-mentioned catalyst combination. The catalyst combinations used in the process according to the invention should have higher CO-shift activities according as the $H_2/CO$ mixtures to be converted have lower $H_2/CO$ molar ratios.

If in the process of the invention the reforming has yielded a $H_2/CO$ mixture with a $H_2/CO$ molar ratio (F) between about 0.25 and about 1.0, then the conversion of this $H_2/CO$ mixture is preferably carried out by using a mixture of two catalysts one of which is the cobalt catalyst and the other a copper and zinc containing composition having a Cu/Zn atomic ratio between about 0.1 and about 10, in which catalyst mixture the two catalysts are present in such a ratio as to satisfy the relation $$0.5 \times \frac{2-F}{1+F} < M < 5 \times \frac{2-F}{1+F},$$

wherein M represents the (Cu+Zn)/Co atomic ratio in the catalyst mixture. By preference, the copper and zinc containing composition has a Cu/Zn atomic ratio between about 0.25 and about 4. Preparatory to being suitable for use the catalyst mixtures should be activated. This activation can suitably be carried out by contacting the catalyst mixture with hydrogen or a hydrogen-containing gas, first at a temperature between about 150° and about 250° C. and next at a higher temperature, between about 200° and about 350° C.

If in the process of the invention the reforming has yielded a $H_2/CO$ mixture with a $H_2/CO$ molar ratio (F) between about 0.75 and about 1.75, then the conversion of this $H_2/CO$ mixture is preferably carried out in two steps, in which in the first step the $H_2/CO$ mixture is partly converted over the cobalt catalyst under such conditions as to satisfy the relation $$150 \times \frac{F - 0.5}{F + 1} < C < 250 \times \frac{F - 0.5}{F + 1},$$

wherein C represents the $H_2+CO$ conversion as %mol, and in which of the product from the first step, after the water formed has been removed, at least the $H_2$ and CO which has remained unconverted is contacted in a second step with a catalyst or catalyst combination which, in addition to activity for the conversion of a $H_2/CO$ mixture into hydrocarbons, has CO-shift activity. In the second step preference is given to the use of a mixture of two catalysts, one catalyst being a cobalt catalyst belonging to the same class as the class from which the cobalt catalyst used in the first step was chosen, and the other catalyst being a copper and zinc containing composition having a Cu/Zn ratio between about 0.1 and about 10. Special preference is given to such catalyst mixtures wherein the two catalysts are present in such a ratio that the (Cu+Zn)/Co atomic ratio of the catalyst mixture lies between about 0.5 and about 5. The copper and zinc containing composition present in the catalyst mixture preferably has a Cu/Zn atomic ratio between about 0.25 and about 4. Preparatory to being suitable for use the catalyst mixtures should be activated in the way described hereinbefore.

As already observed hereinbefore, the present cobalt catalysts when used for the conversion of a $H_2/CO$ mixture yield a substantially waxy product the high-boiling part of which can be converted in high yield into middle distillates by the use of hydrocracking. This also holds when not the cobalt catalysts alone are used, but the above-described catalyst combination which comprise such a cobalt catalyst. Although in the preparation of middle distillates from the products obtained over the cobalt catalyst the part of these products whose initial boiling point lies above the final boiling point of the heaviest middle distillate desired as end product will do as feed for the hydrocracking, it is preferred to use for this purpose the total $C_5+$ fraction of these products, since it has been found that the catalytic hydrotreatment leads to enhanced quality of the gasoline, kerosene and gas oil fractions present therein.

The hydrocracking is carried out be contacting the fraction to be treated at elevated temperature and pressure and in the presence of hydrogen with a catalyst comprising one or more noble metals from Group VIII supported on a carrier. The hydrocracking catalyst used by preference is a catalyst containing about 0.1–2 %w and in particular about 0.2–1 %w of one or more noble metals from Group VIII supported on a carrier. Preference is given to catalysts comprising platinum or palladium as Group VIII noble metal and silica-alumina as carrier. The hydrocracking is preferably carried out at a temperature of about 200°–400° C. and in particular of about 250°–350° C. and a pressure of about 5–100 bar and in particular of about 10–75 bar.

The invention is now illustrated with the aid of the following example which is intended for illustration and not to be construed as limiting the invention.

Feed 1:
A natural gas substantially consisting of methane.

Feed 2:
A natural gas substantially consisting of a mixture of methane and carbon dioxide in a 1:3 volume ratio.

Feed 3:
A natural gas substantially consisting of a mixture of methane and carbon dioxide in a 4:3 volume ratio.

Feed 4:
A natural gas substantially consisting of a mixture of methane and carbon dioxide in a 10:3.5 volume ratio.

Feed 5:
A natural gas substantially consisting of a mixture of methane and carbon dioxide in a 1:1.2 volume ratio.

Catalyst 1:
$Ni/Ca/K/Al_2O_3$ catalyst comprising 13 pbw of nickel, 12 pbw of calcium and 0.2 pbw of potassium per 100 pbw of alumina.

Catalyst 2:
$Co/Zr/SiO_2$ catalyst which comprised 25 pbw of cobalt and 18 pbw of zirconium per 100 pbw of silica and has been prepared by three-step impregnation of a silica carrier with a solution of zirconium tetra n-propoxide in a mixture of n-propanol and benzene, followed by single-step impregnation of the zirconium-loaded carrier with a solution of cobalt nitrate in water. The catalyst had a value for L of 97 mg/ml and for S of 100 $m^2$/ml, and consequently for L/S of 0.97 $mg/m^2$.

Catalyst 3:
$Co/Zr/SiO_2$ catalyst which comprised 25 pbw of cobalt and 0.9 pbw of zirconium per 100 pbw of silica and had been prepared by single-step impregnation of a silica carrier with a solution of cobalt nitrate in water, followed by single-step impregnation of the cobalt-loaded carrier with a solution of zirconium nitrate in water. The catalyst had a value for L of 98 mg/ml and for S of 96 $m^2$/ml and consequently for L/S of 1.02 $mg/m^2$.

Catalyst 4:
$Co/Zr/SiO_2$ catalyst which comprised 25 pbw of cobalt and 12 pbw of zirconium per 100 pbw of silica and had been prepared by three-step impregnation of a silica carrier with a solution of zirconium tetra n-propoxide in a mixture of n-propanol and benzene, followed by impregnation of the zirconium-loaded carrier with a solution of cobalt nitrate in water. The catalyst had a value for L of 97 mg/ml and for S of 100 $m^2$/ml, and subsequently for L/S of 0.97 $mg/m^2$.

In the preparation of Catalysts 2–4 a quantity of solution was used in each impregnation step which substantially corresponded with the pore volume of the carrier, and after each impregnation step the material was dried and then calcined at 500° C.

Catalyst 5:
$Cu/Zn/Al_2O_3$ catalyst which comprised 24.3 %w of copper and 38.0 %w of zinc and consequently had a Cu/Zn atomic ratio of 0.66.

Catalyst Mixture I:
Catalysts 4 and 5 were mixed in such a ratio as to yield a Catalyst Mixture I whose (Cu+Zn)/Co atomic ratio (M) was 1.41.

Six experiments (1–6) were carried out starting from Feeds 1–5. In each of the experiments a feed was converted into a $H_2$ and CO containing reaction product by contacting it, whether or not together with steam, at a temperature of 950° C. and a pressure of 21 bar with Catalyst 1. In Experiments 1 and 4–6 the reaction product was freed from water by cooling and subsequently converted into a mixture of hydrocarbons by contacting it with either one of Catalysts 2 and 3, and/or with Catalyst Mixture I. Preparatory to being used for the hydrocarbon synthesis Catalysts 2 and 3 and Catalyst Mixture I were activated by contacting them with a hydrogen-containing gas, Catalysts 2 and 3 at 250° C. and Catalyst Mixture I first at 200° C. and next at 250° C. Further information on the conditions used to carry out the experiments and the results obtained are given below.

EXPERIMENT 1

Two-step experiment starting from Feed 1.

First step: reforming of Feed 1 in the presence of a quantity of steam corresponding with a $H_2O/CH_4$ molar ratio of 2.0. $CH_4$ conversion achieved: 85.4%. After removal of water 91 %vol. of the reaction product consisted of a $H_2/CO$ mixture with a $H_2/CO$ molar ratio of 4.1.

Second step: the reaction product of the first step which had been freed from water was contacted at a temperature of 220° C., a pressure of 21 bar and a space velocity of 600 Nl $(H_2+CO).1^{-1}.h^{-1}$ with Catalyst 2. The $(H_2+CO)$ conversion achieved was 61 %vol., and the $C_5^+$ selectivity 63%.

EXPERIMENT 2

Single-step experiment starting from Feed 2. In this experiment, in which Feed 2 was reformed without addition of steam, the $CH_4$ conversion was 59%, and the $H_2/CO$ mixture obtained had a $H_2/CO$ ratio of 0.58.

EXPERIMENT 3

Single-step experiment starting from Feed 3. This experiment, in which Feed 3 was reformed in the presence of a quantity of steam corresponding with a $H_2O/CH_4$ molar ratio of 0.35, had to be terminated prematurely on account of clogging of the reactor due to coke formation.

EXPERIMENT 4

Two-step experiment starting from Feed 4.

First step: reforming of Feed 4 in the presence of a quantity of steam corresponding with a $H_2O/CH_4$ molar ratio of 0.8. $CH_4$ conversion achieved: 69%. After removal of water 78 %vol. of the reaction product consisted of a $H_2/CO$ mixture with a $H_2/CO$ molar ratio of 2.

Second step: the reaction product of the first step which had been freed from water was contacted at a temperature of 220° C., a pressure of 21 bar and a space velocity of 600 Nl $(H_2+CO).1^{-1}.h^{-1}$ with Catalyst 2. The $(H_2+CO)$ conversion achieved was 96 %vol., and the $C_5^+$ selectivity 80%.

EXPERIMENT 5

Two-step experiment starting from Feed 2.

First step: reforming of Feed 2 in the presence of a quantity of steam corresponding with a $H_2O/CH_4$ molar ratio of 0.5. $CH_4$ conversion achieved: 96.7%. After removal of water 72 %vol. of the reaction product consisted of a $H_2/CO$ mixture with a $H_2/CO$ molar ratio of 0.55.

Second step: the reaction product of the first step which had been freed from water was contacted at a temperature of 250° C., a pressure of 21 bar and a space velocity of 400 Nl $(H_2+CO).1^{-1}.h^{-1}$ with Catalyst Mixture I. The $(H_2+CO)$ conversion achieved was 83 %vol., and the $C_5^+$ selectivity 83%.

EXPERIMENT 6

Three-step experiment starting from Feed 5.

First step: reforming of Feed 5 in the presence of a quantity of steam corresponding with a $H_2O/CH_4$ molar ratio of 0.5. $CH_4$ conversion achieved: 82.3%. After removal of water 85.5 %vol. of the reaction product consisted of a $H_2/CO$ mixture with a $H_2/CO$ molar ratio of 1.0.

Second step: the reaction product of the first step which had been freed from water was contacted at a temperature of 230° C. and a pressure of 21 bar with Catalyst 3. The reaction product from the second step was divided by cooling into a gaseous fraction substantially consisting of unconverted $H_2$ and CO and $C_4^-$ hydrocarbons, and a liquid fraction substantially consisting of $C_5^+$ hydrocarbons and water. The gaseous fraction was used as feed for the third step.

Third step: the gaseous fraction from step 2 was contacted at a temperature of 260° C. and a pressure of 21 bar with Catalyst Mixture I. Steps 2 and 3 were carried out at a total $(H_2+CO)$ throughput rate of 600 Nl.$1^{-1}.h^{-1}$ and by using Catalyst 3 (in the second step) and Catalyst Mixture I (in the third step) in a 1:2 volume ratio. In this experiment the total $H_2+CO$ conversion was 89% and the total selectivity 83%. The total $H_2+CO$ conversion and the total $C_5^+$ selectivity are defined as follows:

$$\text{Total } H_2 + CO \text{ conversion} = \frac{\text{mol } H_2 + CO \text{ in feed of second step} - \text{mol } H_2 + CO \text{ in product of third step}}{\text{mol } H_2 + CO \text{ in feed of second step}} \times 100$$

$$\text{Total } C_5^+ \text{ selectivity} = \frac{pbw \text{ of } C_5^+ \text{ hydrocarbons in product of second} + \text{third step}}{pbw \text{ of hydrocarbons in product of second} + \text{third step}} \times 100$$

Of Experiments 1–6 described hereinbefore Experiments 4–6 are experiments according to the invention. These experiments, in which the reforming was carried out in the presence of such quantities of carbon dioxide and steam as to satisfy the relation $(2\times a+3\times b)>3$, and in which the synthesis gas formed is subsequently contacted with the special cobalt catalyst or a catalyst combination which comprises the special cobalt catalyst, yielded both a high conversion and a high $C_5^+$ selectivity. Experiments 1–3 fall outside the scope of the invention. They have been included in the patent application for comparison. In Experiment 1 the reforming was carried out in the presence of only steam, and a synthesis gas was obtained which had a high $H_2/CO$ molar ratio. Further processing of this gas in the second step over the special cobalt catalyst led to a low conversion and a low $C_5^+$ selectivity. In Experiment 2 the reforming was carried out in the presence of only carbon dioxide, and a synthesis gas was obtained in low yield which had a low $H_2/CO$ molar ratio. Although further processing of this gas in a second step over the special cobalt catalyst can lead to a high $C_5^+$ selectivity, conversion will only be low. In Experiment 3 the reforming was carried out in the presence of carbon dioxide and steam, but the quantities of carbon dioxide and steam were such that the relation $(2 \times a + 3 \times b) > 3$ was not satisfied. In Experiment 3 there was clogging of the reactor due to coke formation.

We claim:

1. A process for the preparation of $C_5^+$ hydrocarbons suitable for the production of middle distillates from $C_4^-$ hydrocarbons comprising:
   (a) reforming $C_4^-$ hydrocarbons at a pressure higher than 10 bar in the presence of carbon dioxide and steam into a mixture of carbon monoxide and hydrogen having a $H_2/CO$ molar ratio between 0.25 and 2.25 by using a carbon dioxide/hydrocarbon ratio (a) higher than 0.1, but lower than 10 g mol $CO_2$/g atom C, a steam/hydrocarbon ratio (b) higher than 0.1, but lower than 1 g mol $H_2O$/g atoms C and a carbon dioxide/steam ratio chosen such that $(2 \times a + 3 \times b) > 3$, and
   (b) converting the product of (a) into a mixture of hydrocarbons substantially consisting of $C_5^+$ hydrocarbons by contacting it at a temperature of 105°-305° C. and a pressure, substantially corresponding with that used in the reforming, with a cobalt catalyst comprising 3-60 pbw of cobalt and 0.1-100 pbw of at least one other metal chosen from the group formed by zirconium, titanium, and chromium per 100 pbw silica, alumina or silica-alumina, wherein said catalyst has been prepared by kneading and/or impregnation, and that when the $H_2/CO$ mixture has a $H_2/CO$ molar ratio lower than 1.5, the cobalt catalyst is used in a catalyst mixture with a copper and zinc containing composition having CO-shift activity.

2. The process of claim 1, wherein said process is applied to a feed in which the $C_4^-$ hydrocarbons substantially consist of methane.

3. The process of claim 1, wherein said process is applied to natural gas as feed.

4. The process of claim 1, wherein said process is applied to a carbon dioxide contaminated natural gas.

5. The process of claim 1, wherein the reforming is carried out at a temperature of 700°-1000° C., a pressure of 10-75 bar and by using a nickel-containing catalyst.

6. The process of claim 1, wherein at least part of the steam, carbon dioxide or mixtures thereof present in the reaction products of (b) is separated therefrom and is recycled to the reforming step.

7. The process of claim 1, wherein the reforming is carried out by using a carbon dioxide/hydrocarbon ratio higher than 0.3 and lower than 4 g mol $CO_2$/g atom C, and a steam/hydrocarbon ratio higher than 0.2 and lower than 0.8 g mol $H_2O$/g atom C.

8. The process of claim 1, wherein the cobalt catalyst satisfies the relation:

$$(3+4R) > (L/S) > (0.3+0.4R),$$

wherein
L = the total quantity of cobalt present on the catalyst, expressed as mg Co/ml catalyst,
S = the surface area of the catalyst, expressed as m²/ml catalyst, and
R = the weight ratio of the quantity of cobalt deposited on the catalyst by kneading to the total quantity of cobalt present on the catalyst.

9. The process of claim 1, wherein 100 ppw of carrier the cobalt catalyst comprises 15-50 ppw of cobalt and either 0.1-5 ppw of at least one other metal chosen from the group formed by zirconium, titanium and chromium if during its preparation cobalt is deposited first and said other metal next, or 5-40 ppw of at least one other metal if during its preparation said other metal is deposited first and cobalt next.

10. The process of claim 1, wherein the cobalt catalyst comprises zirconium as other metal and silica as carrier.

11. The process of claim 1, wherein (b) is carried out at a pressure of 10-100 bar.

12. The process of claim 1, wherein (b) is carried out at a temperature of 175°-275° C. and pressure of 10-75 bar.

13. The process as claimed in claim 1, wherein in the reforming a $H_2/CO$ mixture is obtained which has a $H_2/CO$ molar ratio (F) between 0.25 and 1.0 and that (b) is carried out by contacting this $H_2/CO$ mixture with a mixture of two catalysts, one of which is the cobalt catalyst and the other a copper and zinc containing composition having a Cu/Zn atomic ratio between 0.1 and 10, whereby in said catalyst mixture the two catalysts are present in a ratio so as to satisfy the relation $$0.5 \times \frac{2-F}{1+F} < M < 5 \times \frac{2-F}{1+F},$$

wherein M represents the (Cu+Zn)/Co atomic ratio in the catalyst mixture.

14. The process of claim 13, wherein the copper- and zinc-containing composition has a Cu/Zn atomic ratio between 0.25 and 4.0.

15. The process of claim 1, wherein in the reforming, a $H_2/CO$ mixture is obtained which has a $H_2/CO$ molar ratio (F) between 0.75 and 1.75 and that (b) is carried out in two steps by partly converting this $H_2/CO$ mixture in the first step over the cobalt catalyst under such conditions as to satisfy the relation $$150 \times \frac{F-0.5}{F+1} < C < 250 \times \frac{F-0.5}{F+1},$$

wherein C represents the $H_2+CO$ conversion as %mol, and after removal of the water formed in the first step of (b), at least the unconverted $H_2$ and CO are contacted in a second step with a catalyst or catalyst combination which in addition to activity for the conversion of a $H_2/CO$ mixture into hydrocarbons has a CO-shift activity.

16. The process of claim 15, wherein in the second step of (b) use is made of a mixture of two catalysts, one of which is the cobalt catalyst and the other a copper and zinc containing composition having a Cu/Zn atomic ratio between 0.1 and 10.

17. The process of claim 15, wherein in the second step of the hydrocarbon synthesis, use is made of a catalyst mixture in which the two catalysts are present such that the (Cu/Zn)/Co atomic ratio in the catalyst mixture lies between 0.5 and 5.

18. The process of claim 15, wherein the copper and zinc containing composition has a Cu/Zn atomic ratio between 0.25 and 4.

19. The process of claim 1, wherein in order to prepare middle distillates from the products prepared over the cobalt catalyst at least the part of said products whose initial boiling point lies above the final boiling point of the heaviest said middle distillates is subjected to hydrocracking by contacting it at elevated temperature and pressure with a catalyst containing one or more noble metals from Group VIII supported on a carrier.

20. The process of claim 19, wherein in the hydrocracking use is made of a catalyst containing 0.2-2 %w of one or more noble metals from Group VIII.

21. The process of claim 20, wherein in the hydrocracking use is made of a catalyst containing 0.2-1 %w of one or more noble metals from Group VIII.

22. The process of claim 19, wherein in the hydrocracking use is made of a catalyst containing platinum or palladium as Group VIII noble metal and silica-alumina as carrier.

23. The process of claim 19, wherein the hydrocracking is carried out at a temperature of 200°-400° C. and a pressure of 5-100 bar.

24. The process of claim 23, wherein the hydrocracking is carried out at a temperature of 250°-350° C. and a pressure of 10-75 bar.

* * * * *